US 6,630,605 B2

(12) United States Patent
Wegner et al.

(10) Patent No.: US 6,630,605 B2
(45) Date of Patent: Oct. 7, 2003

(54) PROCESS FOR THE PURIFICATION OF PHOSPHONIUM SALTS

(75) Inventors: Christoph Wegner, Kirchheim (DE); Daniela Klein, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/161,682

(22) Filed: Jun. 5, 2002

(65) Prior Publication Data

US 2002/0193637 A1 Dec. 19, 2002

(30) Foreign Application Priority Data

Jun. 19, 2001 (DE) .......................... 101 29 403

(51) Int. Cl.$^7$ .................................. C07F 9/54

(52) U.S. Cl. .......................... 568/9; 210/660

(58) Field of Search ................ 568/9; 210/660

(56) References Cited

U.S. PATENT DOCUMENTS

| | | | | | |
|---|---|---|---|---|---|
| 3,432,559 | A | * | 3/1969 | Ludwig ........................ | 568/9 |
| 3,466,335 | A | * | 9/1969 | Ruegg et al. .................. | 568/9 |
| 3,932,485 | A | * | 1/1976 | Surmatis ..................... | 560/128 |
| 4,098,827 | A | * | 7/1978 | Rosenberger ................ | 568/824 |
| 4,122,123 | A | * | 10/1978 | Hestermann et al. .......... | 568/9 |
| 4,182,731 | A | * | 1/1980 | Schulz et al. ................ | 568/9 |
| 5,166,445 | A | * | 11/1992 | Meyer ........................ | 568/2 |
| 6,169,209 | B1 | * | 1/2001 | Harada et al. ................ | 568/9 |
| 6,187,959 | B1 | * | 2/2001 | Wegner et al. ............... | 568/9 |
| 6,423,873 | B1 | * | 7/2002 | Wegner et al. ............... | 568/9 |

* cited by examiner

Primary Examiner—Jean F. Vollano
(74) Attorney, Agent, or Firm—Keil & Weinkauf

(57) ABSTRACT

The invention relates to a process for the purification of phosphonium salts in which a solution of the crude phosphonium salt is passed over a bed of a cation exchange resin in salt form or of an adsorber resin, the resin is washed with a polar protic solvent in the case of the cation exchange resin and with an electrolyte solution and a nonpolar solvent in the case of the adsorber resin, and the phosphonium salt is eluted from the cation exchange resin with an electrolyte solution or from the adsorber resin with a polar solvent.

13 Claims, No Drawings

PROCESS FOR THE PURIFICATION OF PHOSPHONIUM SALTS

The present invention relates to a process for the purification of phosphonium salts which have a hydrocarbon radical with 5 to 40 carbon atoms, in particular ionylideneethylphosphonium salts such as 3,7,11-trimethyldodeca-2,4,6,10-tetraen-1-ylphosphonium salts.

To prepare carotenoids in many cases phosphonium salts and aldehydes are reacted in a Wittig reaction. Thus, to synthesize lycopene, a red pigment which occurs as natural carotenoid in tomatoes, 3,7,11-trimethyldodeca-2,4,6,10-tetraen-1-ylphosphonium salts are reacted for example with 2,7-dimethyl-2,4,6-octatrienedial. β-Ionylideneethylphosphonium salts can be converted correspondingly into β-carotene and 2-hydroxy-β-ionylideneethylphosphonium salts can be converted correspondingly into zeaxanthin etc.

EP 0 382 067 describes the preparation of 3,7,11-trimethyldodeca-2,4,6,10-tetraen-1-ylphosphonium salts by reacting 3,7,11-trimethyldodeca-1,4,6,10-tetraen-3-ol with at least one equivalent of triarylphosphine in an inert solvent in the presence of a $C_1$–$C_6$-alkanoic acid or boron trifluoride-etherate. The phosphonium salt which is initially produced can be converted into the chloride, bromide, sulfate, hydrogen sulfate, phosphate or a sulfonate.

No simple process for the purification of the phosphonium salts, in particular for removing the phosphine which is employed in excess, or the acid.

It is an object of the present invention to provide a process which makes it possible to purify the crude phosphonium salts simply and effectively.

We have found that this object is achieved by use of a solid phase. The use of a solid phase has the advantage over processes of purification by extraction from one liquid phase into another liquid phase that any solvent can be used without the need to ensure the formation of two phases.

In a first aspect, the invention relates to a process for the purification of phosphonium salts of the formula

in which R is a hydrocarbon radical with 5 to 40 carbon atoms, R' is $C_1$–$C_4$-alkyl or $C_6$–$C_{10}$-aryl and X is an equivalent of an anion, in which
 a) a solution of the crude phosphonium salt is passed over a bed of a cation exchange resin in salt form,
 b) the cation exchange resin is washed with at least one polar protic or aprotic and/or at least one nonpolar solvent, preferably with at least one polar protic and at least one nonpolar solvent in any sequence, and
 c) the phosphonium salt is eluted from the cation exchange resin with an electrolyte solution, where appropriate in combination with a polar aprotic solvent.

In a second aspect, the invention relates to a process for the purification of phosphonium salts of the formula

in which R, R' and X have the meanings indicated above, in which
 a) a solution of the crude phosphonium salt is passed over a bed of an adsorber resin,
 b) the adsorber resin is washed with at least one nonpolar solvent and/or at least one electrolyte solution, preferably with at least one nonpolar solvent and at least one electrolyte solution in any sequence, and
 c) the phosphonium salt is eluted from the adsorber resin with a polar protic or aprotic solvent.

X is an equivalent of an anion such as halide, e.g. chloride or bromide, sulfate, phosphate, a sulfonate such as benzenesulfonate or toluenesulfonate, $C_1$–$C_6$-alkanoate, in particular acetate, or hydroxytrifluoroborate.

"$C_6$–$C_{10}$-Aryl" is preferably phenyl or tolyl, in particular phenyl.

The radical R is a linear, branched and/or cyclic hydrocarbon radical with 5 to 40 carbon atoms, preferably 10 to 20 carbon atoms, in particular 15 carbon atoms. It may comprise one or two heteroatoms, in particular oxygen atoms. If the radical R comprises a hydroxyl group, this may be protected by conventional hydroxyl protective groups such as those mentioned hereinafter as R". The process of the invention is particularly suitable for the purification of phosphonium salts employed for synthesizing carotenoids by the Wittig reaction, i.e. those phosphonium salts in which R comprises one to 8 isoprene units, preferably 2 to 4 isoprene units, in particular 3 isoprene units.

Typical examples of R are the following radicals of the formulae Ia–Ik (in which R" is hydrogen or a hydroxyl protective group, such as acyl, e.g. acetyl, propionyl or benzoyl; alkyl, e.g. methyl, ethyl or t-butyl; silyl, e.g. t-butyldimethylsilyl; or alkoxyalkyl, e.g. 2-methoxy-2-propyl or tetrahydropyranyl):

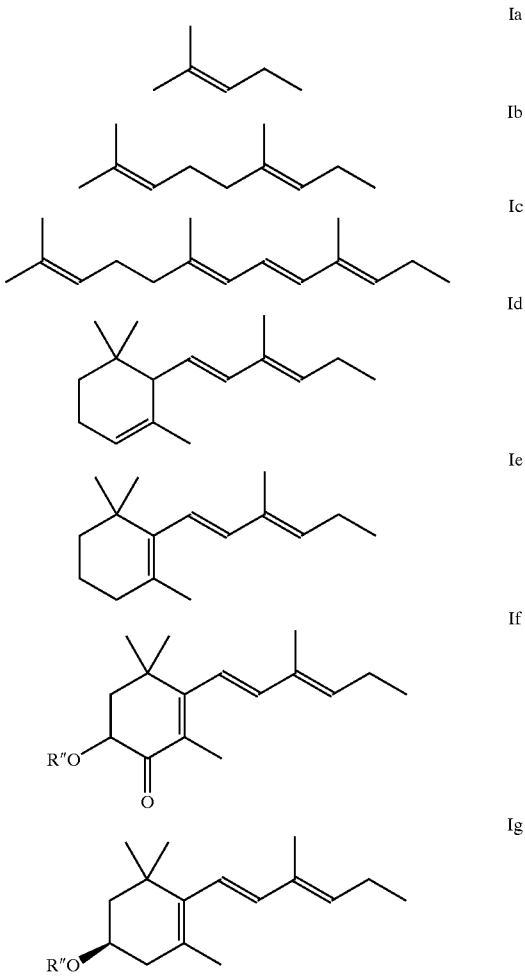

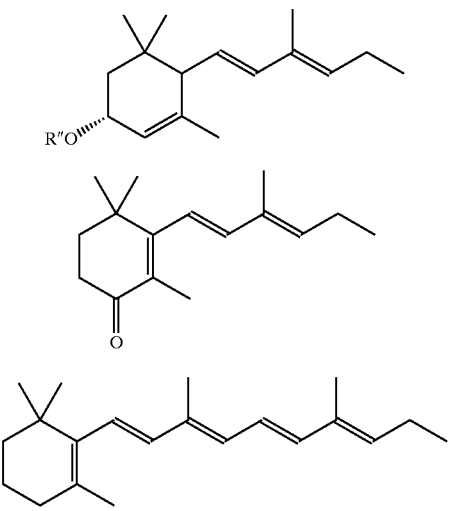

R is preferably an ionylideneethyl radical. The term "ionylideneethyl" is intended to be understood in its broadest possible meaning and to include all $C_{15}$ radicals which are distinguished from naturally occurring ionones by two carbon atoms and/or can be regarded as degradation products of naturally occurring carotenoids. These include, in particular, ψ-ionylideneethyl or pseudoionylideneethyl (3,7,11-trimethyldodeca-2,4,6,10-tetraen-1-yl; Ic), α-ionylideneethyl (Id), β-ionylideneethyl (Ie), 3-hydroxy-4-keto-β-ionylideneethyl (If, R"=H), 3-hydroxy-β-ionylideneethyl (Ig, R"=H), 3-hydroxy-α-ionylideneethyl (Ih, R"=H), 4-keto-β-ionylideneethyl (Ij).

The phosphonium salts can be prepared in a variety of ways. If R is an ionylideneethyl radical, they are expediently obtained by reacting the corresponding vinylionol with at least one mole equivalent of phosphine of the formula $PR'_3$ in a solvent in the presence of an acid. The vinylionols can in turn be obtained, for example, from ionones by vinyl Grignard reaction.

Thus, a phosphonium salt in which R is a radical of the formula Ic is expediently obtained by reacting 3,7,11-trimethyldodeca-1,4,6,10-tetraen-2-ol with the phosphine and the acid.

The phosphine is preferably used in excess, e.g. 1.1 to 3 equivalents. Triarylphosphines are preferred, and triphenylphosphine is most preferred. The acid is preferably employed in an excess of at least 3, in particular at least 8, equivalents. Suitable acids are $C_1$–$C_6$-alkanoic acids, boron trifluoride-etherate, hydrochloric acid, hydrobromic acid, phosphoric acid or a sulfonic acid such as benzenesulfonic acid or toluenesulfonic acid. If an alkanoic acid such as acetic acid is used as acid, this is expediently also employed as solvent.

The process of the invention starts from a solution of the crude phosphonium salt in a solvent such as optionally chlorinated or aromatic hydrocarbons, ethers, alcohols or esters, such as hexane, dichloromethane, trichloromethane, benzene, toluene, xylene, diisopropyl ether, tetrahydrofuran, methanol, ethanol and the like. The crude phosphonium salt is particularly preferably dissolved in a $C_1$–$C_6$-alkanoic acid, in particular acetic acid, or a mixture thereof with water.

The cation exchanger according to the first aspect of the invention is preferably a strongly acidic cation exchanger, which may be macroporous or in gel form, with low or high crosslinkage. Ion exchangers based on polystyrene with sulfo groups have proved particularly suitable. Such ion exchangers are commercially available for example under the name S1468, S100 from Bayer or the name Amberlite IR-120, Amberlite 200 from Rohm and Haas. Before loading of the phosphonium salt to be purified, the cation exchanger is converted into the salt form, i.e. a form in which the anionic groups which are covalently bonded to the resin are associated with metal cations, preferably alkali metal cations, in particular sodium ions. If the cation exchanger is not already in salt form, this can be effected in a simple manner by passing an aqueous solution of a metal hydroxide over the bed of cation exchanger.

The adsorber resin according to the second aspect of the invention preferably has an average pore size of from 50 to 100 Å, in particular 60 to 100 Å. Suitable adsorber resins are, inter alia, those based on polystyrene or polyacrylate. Polyacrylate adsorber resins are preferred. Suitable resins are commercially available under the name XAD2, XAD4, XAD7, XAD16 from Rohm and Haas.

To carry out the process of the invention, a commercially available chromatography column is packed in a conventional way with an ion exchange or adsorber resin suitable according to the invention. The resin material can, for example, be suspended in water and then introduced into the column. The material is then compacted in a suitable way and fixed with the aid of a retaining element. The column is then pretreated in a conventional way by washing and equilibrating the resin.

The crude phosphonium salt solution and the solvents and eluents can be passed in the direction of gravity or opposite to the direction of gravity over the bed of the cation exchanger or of the adsorber resin. The liquids are preferably passed opposite to the direction of gravity through the bed in order to prevent compaction of the bed and a rise in pressure associated therewith. It is advantageous to use for this purpose a diaphragm pump whose delivery side is connected to the lower end of the chromatography column.

The prepared chromatography column is next loaded with a solution of the phosphonium salt to be purified at a low pumping rate. The temporary binding to the resin material is based in the case of a cation exchanger on an ionic bonding of the phosphonium cations to the anionic anchor groups of the ion exchanger, and in the case of a polymer resin on a reversible adsorption effect.

After loading the column, the unwanted constituents are removed by washing with suitable washing liquids. In the process according to the first aspect of the invention, the washing with the polar protic solvent serves to remove polar impurities such as, for example, excess alkanoic acid, and the washing with the nonpolar solvent serves to remove nonpolar impurities such as, for example, excess phosphine. In the process according to the second aspect of the invention, the removal of polar impurities takes place by washing with an electrolyte solution. The presence of the electrolyte is necessary in order to reduce the solubility of the phosphonium salt, because the latter would otherwise be eluted prematurely.

Suitable polar protic solvents are those having a dielectric constant DC of from 40 to 110 (concerning the determination of the dielectric constant, reference is made to the CRC Handbook of Chemistry and Physics, CRC Press, 76th edition, pp. 6–159 to 6–192) and having at least one hydrogen atom bonded to an oxygen or nitrogen atom. These include, in particular, water and $C_1$–$C_4$-alkanols such as methanol or ethanol.

Suitable nonpolar solvents are those having a DC of from 1 to 7. These include, in particular, aliphatic hydrocarbons such as hexane, heptane, petroleum ether, or diethyl ether.

Suitable polar aprotic solvents are those having a dielectric constant DC of from 7 to 70. These include, in particular, halogenated hydrocarbons such as dichloromethane, trichloromethane, tetrachloromethane, dichloroethylene, trichloroethylene, dichloroethane, trichloroethane, tetrahydrofuran, dioxane or dimethyl sulfoxide. Of these, dichloromethane is preferred.

Suitable electrolyte solutions are solutions of salts in water, $C_1$–$C_4$-alkanols or mixtures thereof. Suitable salts are, in particular, alkaline earth or alkali metal halides, e.g. chlorides, sulfates or $C_1$–$C_6$-alkanoates. The sodium and potassium salts are generally preferred. Sodium chloride is most preferred. The salt concentration is preferably from at least 2% by weight up to the saturation limit, usually 5 to 25% by weight.

The purified phosphonium salt is recovered by washing the column with a suitable eluent. In the process according to the first aspect of the invention, the product is eluted with an electrolyte solution. The electrolyte solution may, where appropriate, be used in combination with a polar aprotic solvent. The electrolyte solution and the polar aprotic solvent can be applied as mixture or alternately in any sequence, optionally in a plurality of portions. If the solvent is immiscible with the electrolyte solution, the organic phase of the eluate is expediently separated off and evaporated to the desired concentration. In the second aspect of the invention, a polar solvent, preferably an aprotic polar solvents is used for the elution. The eluate can then be evaporated to the desired concentration. The process generally gives yields of more than 70%.

The present invention is now illustrated further by the following examples. The yield of purified phosphonium salts and the ratios of E to Z isomers were determined by high pressure liquid chromatography (HPLC) using internal standards. In the examples, the phosphonium salt solution and the solvents for washing and eluting were passed from bottom to top of the chromatography column by means of a diaphragm metering pump.

EXAMPLE 1

320 ml of cation exchange material (Bayer Lewatit K2641) moistened with water were packed into a chromatography column. The material was thoroughly compacted and fixed with the aid of a variable endpiece. Then 150 g of crude triphenyl-(3,7,11-trimethyldodeca-2,4,6,10-tetraen-1-yl)phosphonium salt (about 26% pure; dissolved in 70% by weight aqueous acetic acid) with a ratio of E to Z isomers of 4.17 were loaded onto the column from the bottom at a pumping rate of 150 ml/h. The column was then washed with 1.35 l of deionized water to remove the acetic acid. The pumping rate during the washing step was 1500 ml/h. Unreacted triphenylphosphine was removed by subsequent washing with 1.0 l of n-heptane. The pumping rate was 1500 ml/h.

The purified product was eluted from the ion exchange material four times alternately with 250 ml of NaCl solution (10% strength) and 250 ml of dichloromethane each time, and the phases were separated. The organic phase was concentrated to an approximately 25% strength solution.

The product was determined by HPLC analysis. This showed that 27.6 g of purified $C_{15}$-phosphonium salt with an E/Z ratio of 4.24 were obtained. The yield was 71% of theory.

EXAMPLE 2

A chromatography column was packed with 320 ml of polyacrylate-based adsorber material (Rohm and Haas Amberlite XAD7) moistened with water. The material was thoroughly compacted and fixed by means of a variable endpiece. Then 150 g of crude triphenyl-(3,7,11-trimethyldodeca-2,4,6,10-tetraen-1-yl)-phosphonium salt (about 26% pure; dissolved in 70% by weight aqueous acetic acid) with a ratio of E to Z isomers of 4.22 were loaded onto the column at a pumping rate of 150 ml/h. The column was then washed with 1.35 l of 10% NaCl solution to remove the acetic acid, the pumping rate being 1500 ml/h. Unreacted triphenylphosphine was removed by subsequent washing with 1.5 l of n-heptane. The pumping rate was 1500 ml/h.

The purified product was eluted from the adsorber material with 1.5 l of dichloromethane, and the eluate was concentrated to an approximately 25% strength solution.

The product was determined by HPLC analysis. This showed that 29.4 g of purified $C_{15}$-phosphonium salt with an E/Z ratio of 4.22 were obtained. The yield was 75% of theory.

EXAMPLE 3

A chromatography column was packed with 350 ml of water-moist cation exchanger (Dowex 50 WX 2), and the material was thoroughly compacted and fixed by means of a variable endpiece. 100 g of crude triphenyl-(3,7,11-trimethyldodeca-2,4,6,10-tetraen-1-yl)-phosphonium salt (about 23% pure; dissolved in 70% by weight aqueous acetic acid) with an E/Z ratio of 4.17 were pumped onto the column at a pumping rate of 150 ml/h. The acetic acid was then removed by washing with 0.9 l of deionized water (pumping rate 1500 ml/h) and the triphenylphosphine was removed by washing with 1.0 l of n-heptane (pumping rate 1500 ml/l). The purified product was eluted from the ion exchange material four times alternately with 250 ml of NaCl solution (10% strength) and 250 ml of dichloromethane each time, the phases were separated, and the organic phase was concentrated to an approximately 25% strength solution. 15.9 g of purified $C_{15}$-phosphonium salt with an E/Z ratio of 4.18 according to HPLC analysis were isolated (69% of theory).

EXAMPLE 4

A chromatography column was packed with 350 ml of water-moist polystyrene-based adsorber resin (Rohm and Haas Amberlite XAD16), and the material was thoroughly compacted and fixed by means of a variable endpiece. 100 g of crude triphenyl-(3,7,11-trimethyldodeca-2,4,6,10-tetraen-1-yl)phosphonium salt (about 23% pure; in 70% by weight aqueous acetic acid) with an E/Z ratio of 4.22 were pumped onto the column at apumping rate of 150 ml/h. The acetic acid was removed by washing with 900 ml of NaCl solution (10% strength) (pumping rate 1500 ml/h) and the triphenylphosphine was removed by washing with 1.0 l of heptane (pumping rate 1500 ml/h). The purified product was eluted from the adsorber material with 1.5 l of dichloromethane and concentrated to an approximately 25% strength solution. 16.8 g of purified $C_{15}$-phosphonium salt with an E/Z ratio of 4.19 according to HPLC analysis were isolated (73% of theory).

We claim:

1. A process for the purification of phosphonium salts for the formula

in which R is a hydrogen radical with 5 to 40 carbon atoms, $R^1$ is $C_1$–$C_4$-alkyl or $C_6$–$C_{10}$-aryl and X is an equivalent of and anion, in which a) a solution of the crude phosphonium salt is passed over a bed of a cation exchange resin in salt form, b) the cation exchange resin is washed with at least one polar protic or aprotic and/or at least one nonpolar solvent, and c) the phosphonium salt is eluted form the cation exchange resin with an electrolyte solution, optionally in combination with a polar aprotic solvent.

2. A process as claimed in claim 1, where R comprises one to 8 isoprene units.

3. A process as claimed in 2, where R is an ionylideneethyl radical.

4. A process as claimed 3, where R is 3, 7, 11-trimethyldodeca-2,4,6,10-tetraen-1-yl.

5. A process as claimed in claim 1, where the polar protic solvent is selected from water and $C_1$–$C_4$-alkanols and the nonpolar solvent is selected from aliphatic hydrocarbons and diethyl ether.

6. A process as claimed in claim 1, where the polar aprotic solvent is selected from halogenated hydrocarbons, tetrahydrofuran, dioxane and dimethyl sulfoxide.

7. A process as claimed is claim 1, where the electrolyte solution is an aqueous sodium chloride solution.

8. A process for the purification of phosphonium salts of the formula

in which R, R' and X have the meanings indicated in claim 1, in which a) a solution of the crude phosphonium salt is passed over a bed of an absorber resin selected from the group consisting of a polyacrylate or polystyrene adsorber resin, b) the adsorber resin is washed with at least one nonpolar solvent and/or at least one electrolyte solution, and c) the phosphonium salt is eluted from the adsorber resin with a polar solvent.

9. A process as claimed in claim 8, where R comprises one to 8 isoprene units.

10. A process as claimed in claim 9, where R is an ionylideneethyl radical.

11. A process as claimed in claim 10, where R is 3,7,11-trimethyldodeca-2,4,6,10-tetraen-1-yl.

12. A process as claimed in claim 8, where the nonpolar solvent is selected from aliphatic hydrocarbons and diethyl ether, and the electrolyte solution is an at least 2% by weight, aqueous sodium chloride solution.

13. A process as claimed in claim 8, where the polar solvent is selected from halogenated hydrocarbons, tetrahydrofuran, dioxane and dimethyl sulfoxide.

* * * * *